United States Patent
Levasseur

(10) Patent No.: US 12,097,060 B2
(45) Date of Patent: Sep. 24, 2024

(54) LONG AXIS IMAGING SYSTEM AND METHOD

(71) Applicant: Medtronic Navigation, Inc., Louisville, CO (US)

(72) Inventor: Elizabeth A. Levasseur, New Boston, NH (US)

(73) Assignee: Medtronic Navigation, Inc., Lafayette, CO (US)

(*) Notice: Subject to any disclaimer, the term of this patent is extended or adjusted under 35 U.S.C. 154(b) by 303 days.

(21) Appl. No.: 17/590,202

(22) Filed: Feb. 1, 2022

(65) Prior Publication Data

US 2023/0240632 A1    Aug. 3, 2023

(51) Int. Cl.
*A61B 34/20* (2016.01)
*A61B 6/00* (2006.01)
*A61B 6/04* (2006.01)

(52) U.S. Cl.
CPC .......... *A61B 6/4476* (2013.01); *A61B 6/0407* (2013.01); *A61B 6/4405* (2013.01); *A61B 6/4452* (2013.01); *A61B 6/54* (2013.01); *A61B 34/20* (2016.02); *A61B 2034/2051* (2016.02); *A61B 2034/2055* (2016.02); *A61B 2034/2063* (2016.02)

(58) Field of Classification Search
CPC ..... A61B 6/4476; A61B 34/20; A61B 6/0407; A61B 6/4405; A61B 6/4452; A61B 6/54; A61B 2034/2051; A61B 2034/2055; A61B 2034/2063
See application file for complete search history.

(56) References Cited

U.S. PATENT DOCUMENTS

| | | | |
|---|---|---|---|
| 5,592,939 A | 1/1997 | Martinelli | |
| 5,772,594 A | 6/1998 | Barrick | |
| 5,913,820 A | 6/1999 | Bladen et al. | |
| 5,983,126 A | 11/1999 | Wittkampf | |
| 7,001,045 B2* | 2/2006 | Gregerson | A61N 5/1082 378/197 |
| 7,108,421 B2* | 9/2006 | Gregerson | A61B 6/4405 378/146 |
| 7,751,865 B2 | 7/2010 | Jascob et al. | |
| 8,842,893 B2 | 9/2014 | Teichman et al. | |
| 9,737,235 B2 | 8/2017 | Hartmann | |
| 2004/0199072 A1 | 10/2004 | Sprouse et al. | |
| 2006/0120511 A1* | 6/2006 | Gregerson | A61B 6/4429 378/198 |
| 2019/0099141 A1* | 4/2019 | Garlow | A61B 6/4411 |

FOREIGN PATENT DOCUMENTS

WO     0110300 A1    2/2001

OTHER PUBLICATIONS

International Search Report and the Written Opinion of the EPO/International Searching Authority, corresponding to PCT/US2023/011431, Mailing Date: Mar. 24, 2023.

* cited by examiner

*Primary Examiner* — David P Porta
*Assistant Examiner* — Fani Polyzos Boosalis
(74) *Attorney, Agent, or Firm* — Harness, Dickey & Pierce, P.L.C.

(57) ABSTRACT

Disclosed is a system and method for operating an imaging system. The imaging system may move or be moved to acquire image data of a subject at different positions relative to the subject. The image data may, thereafter, be combined to form a single image.

21 Claims, 10 Drawing Sheets

LONG AXIS IMAGING SYSTEM AND METHOD

FIELD

The present disclosure relates to an imaging system, and particularly to a moveable imaging system and acquisition of image data therewith.

BACKGROUND

Imaging systems may acquire image data of a subject. The image data is used to generate images. The images may be displayed for viewing by a user and/or further analyzed and/or augmented for various purposes. The images may illustrate a selected portion(s) of a subject.

An imaging system that acquires image data of the subject may acquire a plurality of image data projections of the subject. The plurality of projections may be acquired at a plurality of positions of the imaging system relative to the subject. For example, a system may include an arm or a projector that moves in space relative to a subject to acquire a plurality of positions of image projections relative to the subject.

Further areas of applicability will become apparent from the description provided herein. The description and specific examples in this summary are intended for purposes of illustration only and are not intended to limit the scope of the present disclosure.

SUMMARY

This section provides a general summary of the disclosure, and is not a comprehensive disclosure of its full scope or all of its features.

An imaging system may include a portion that moves relative to a selected position. A subject may be placed at the position for acquiring image projections thereof. The imaging system may acquire one or a plurality of image projections, including image data, at a plurality positions relative to the subject.

The plurality of image projections may be acquired to generate a long image of the subject. For example, the imaging portion of the imaging system may translate axially (i.e., along a Z-axis) relative to the subject to acquire image projections at a plurality of positions along the axis. As the imaging portion moves, the imaging portion may move relative to the subject while a selected portion of the imaging system may remain stationary.

The imaging system may further include a moveable base. The moveable base allows the imaging system as a whole to move from one location to another location. The imaging system, therefore, may be a mobile imaging system for use in multiple locations.

The imaging portion of the imaging system may include an x-ray emitter and a x-ray detector. The emitter and detector may be moveable within a gantry. The gantry may be moveable relative to the base. The gantry may move via a telescoping track system to allow for a selected and extended range along a selected axis. The telescoping track, however, may maintain the gantry in a selected orientation relative to the subject during the movement of the gantry. Thus, the base may be moved to a selected location. The base may be fixed at the selected location. The gantry may then move relative to the subject by the telescoping track to acquire a plurality of image projections of the subject along a long axis of the subject. The gantry may move at least about 50 centimeters (cm) to about 77 cm along the long axis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 8:
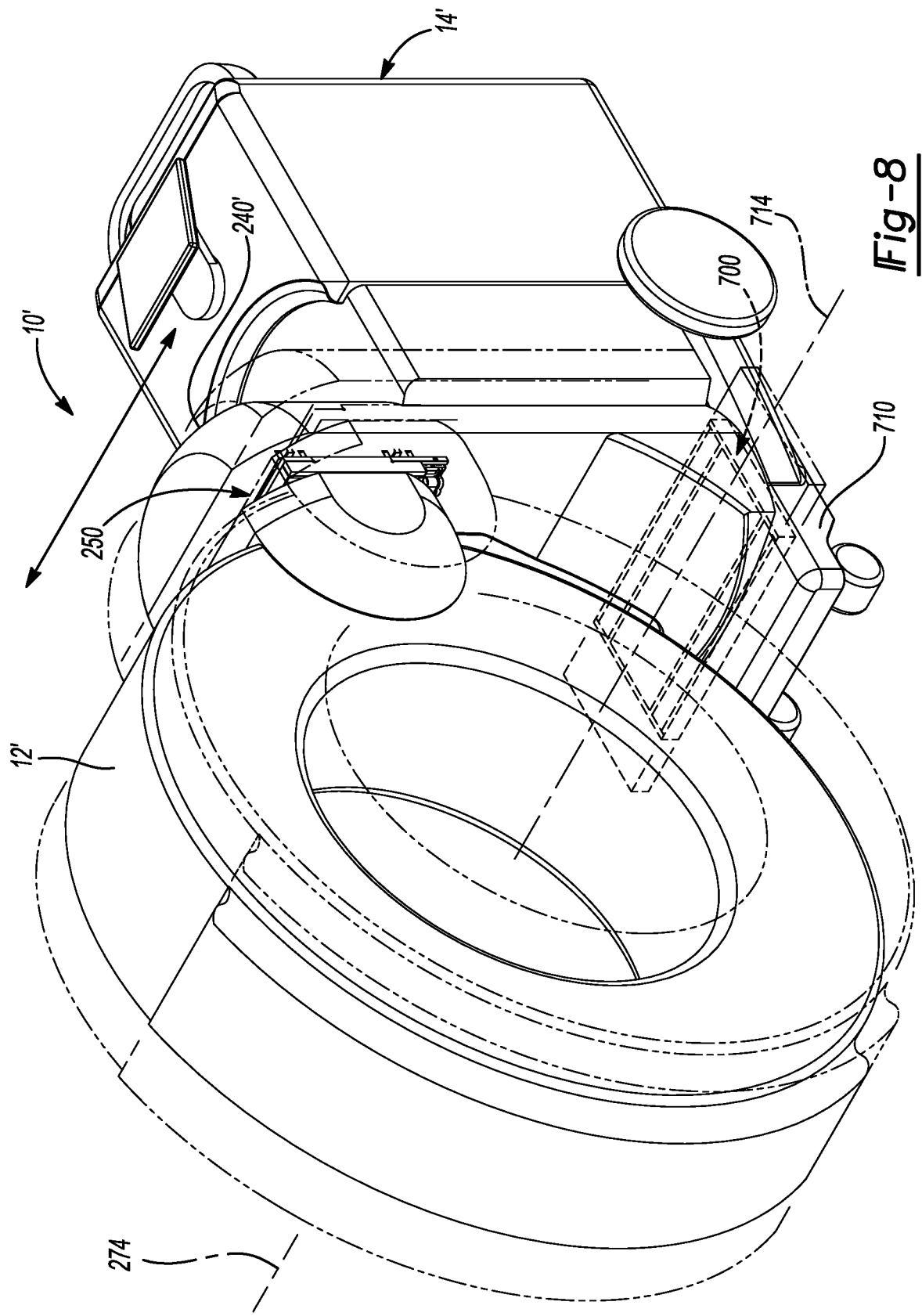

FIG. 8 perspective view of an imaging system with a gantry in three positions, shown in phantom, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
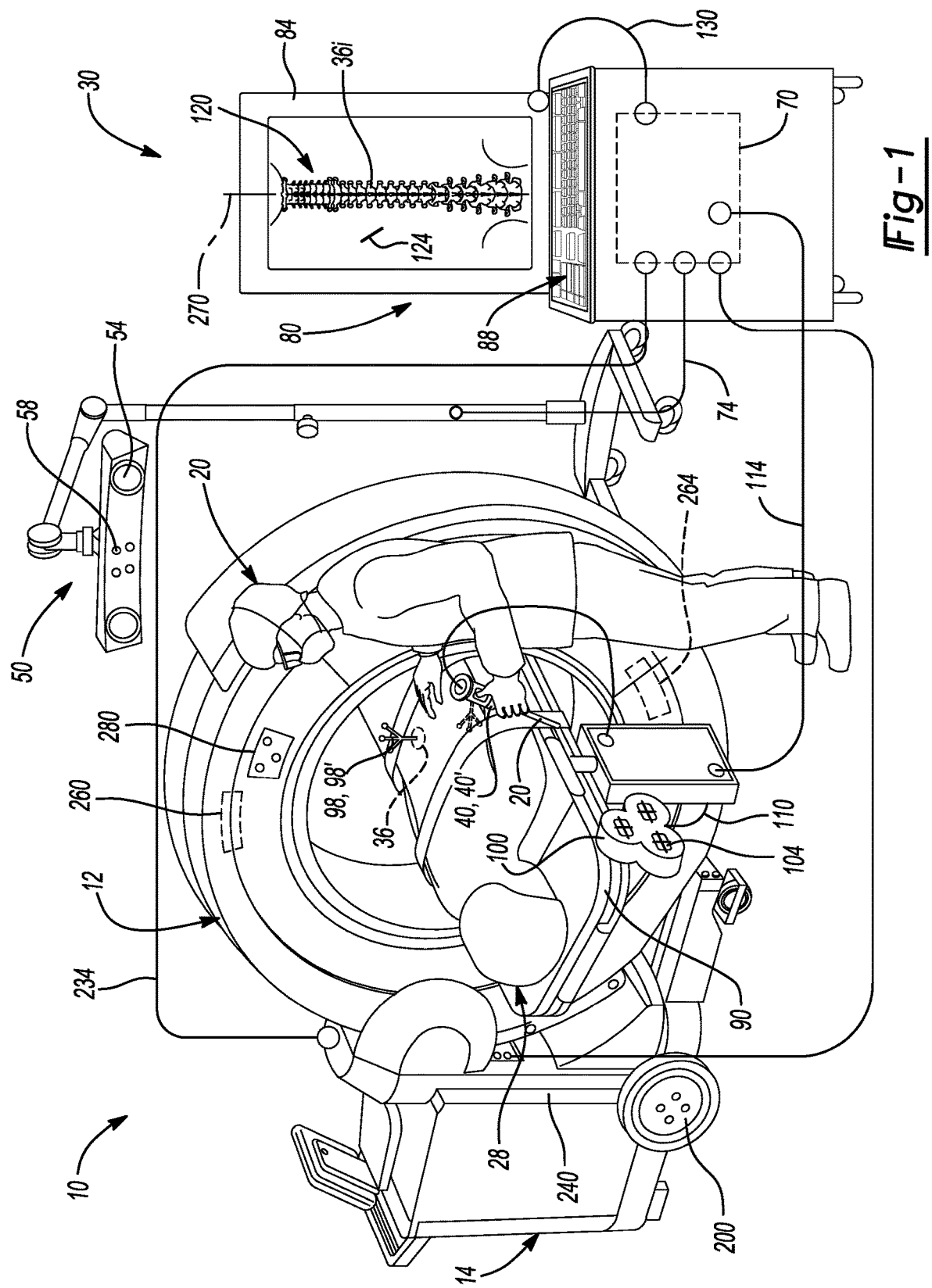
FIG. 1 is an environmental view of a procedure room with an imaging system and navigation system, according to various embodiments.

FIG. 1 is an environmental view of a procedure area and system that may be used during a procedure. During a procedure, an imaging system 10 may be used to acquire image data of a subject (e.g. patient) 28, as discussed further herein. With additional reference to FIGS. 2A, 2B, and 2C, the imaging system 10 may be operated to acquire a long image of a subject 28. The imaging system 10 includes a gantry 12 that may move along an axis 28a of the subject 28 relative to a moveable base 14. As discussed herein, the movement of the gantry allows for an extended image of the subject to be generated based on the image data acquired with the imaging system 10. Thus, a single image acquisition may be used to acquire image data sufficient to generate an image of a portion of the subject having a long axis length of about 50 centimeters (cm) to about 80 cm.

In addition, the procedure area may include an instrument 20 (e.g., a powered drill assembly, tap, reamer, etc.) to be used by a user 24, to perform a procedure on the subject 28. In various embodiments, the instrument 20 may include a powered dissection tool for performing a select procedure, such as forming a burr hole in a cranium of the subject 28, operating on one or more a vertebra 36, or other selected procedure. The instrument 20, according to various embodiments, may include any appropriate motor component such as the LEGEND MR8® and/or LEGEND EHS STYLUS® motor systems, sold by Medtronic, Inc. The motor component may include a motor that is powered such as pneumatic powered, as the LEGEND MR7® motors, although other power motors or drives may be used such as electric power motors LEGEND EHS STYLUS® motors. It is understood, however, that the powered drill assembly 20 may be used for performing other procedures such as a removal of material relative to and/or in the vertebrae.

In various embodiments of a procedure, the instrument 20 may be operated to remove a portion of the vertebra in a selected procedure, including a laminectomy procedure or other appropriate spinal procedure. Further, it is understood that the instrument 20 may be used to perform a procedure on a non-living subject such as to drill a hole in an airframe, an automotive frame, or the like. Accordingly, the instrument 20 is not required to be used with a living subject, such as a human patient.

The imaging system 10 may be used prior to, during, or after any selected portion of the procedure. In various embodiments, for example, the imaging system 10 may be used to acquire image data of the subject 28 to assist in and/or plan for the procedure. In various embodiments, the image data may be used to assist in navigating a procedure on the subject 28.

A navigation system 30 may include a tracking system, as discussed further herein, and may include a tracking device 40 that may be connected to the instrument 20 to track a position or pose of instrument 20 relative to the subject 28, such as the vertebra 36. Generally, the pose includes both a coordinate location (such as a location in 3D space) and an orientation (such as at least one or more, including three, degrees of freedom). Thus, a pose or position may include a selected amount of degrees of freedom, such as six degrees of freedom information regarding an object (e.g., the instrument 20). Appropriate tracking systems include those disclosed in U.S. Pat. No. 8,842,893, incorporated herein by reference.

To acquire the image data, the imaging system 10 may be used prior to beginning a procedure or after a procedure has begun, the procedure may include operation of the instrument 20. The imaging system 10 may include portions of an O-arm® imaging system sold by Medtronic, Inc. and/or may include imaging system portions such as those disclosed in U.S. Pat. Nos. 7,188,998; 7,108,421; 7,106,825; 7,001,045; and 6,940,941; all of which are incorporated herein by reference. Other possible imaging systems include C-arm fluoroscopic imaging systems which can also generate three-dimensional views of the patient 28, such as the ZIEHM VISION® RFD 3D imaging system sold by Ziehm Imaging GmbH having a place of business at Nuremberg, Germany.

The tracking system may be a part of the navigation system 30 to assist in performing selected procedures, such as a surgical procedure on the subject 28, and may include those as generally known in the art. For example, navigation systems may include those as disclosed in U.S. Pat. Nos. 5,772,594; 5,913,820; 5,592,939; 5,983,126; 7,751,865; and 8,842,893; and 9,737,235 and those disclosed in U.S. Pat. App. Pub. No. 2004/0199072, all incorporated herein by reference. Tracked positions may be displayed on images or relative to images due to registration of a position of a subject or real space to an image space, also as disclosed in the U.S. patents and publications as incorporated above. Further, tracking systems may include the Stealth Station® S8® tracking system, and AxiEM™ tracking system, all sold by Medtronic Navigation, Inc.

The tracking systems may include various features such as an optical tracking systems, EM tracking systems, ultrasonic tracking systems, or the like. Nevertheless, as illustrated in FIG. 1, for example, a tracking system may include one or more localizers that may include portions that include cameras and/or antennas for receiving/and or transmitting a signal for tracking. Localizers may include an optical localizer 50 that includes one or more cameras 54 that may detect or "view" the tracking device 40 connected to the instrument 20. The localizer 50 including the cameras 54 may emit a selected radiation, such as infrared radiation from emitters 58, that is reflected by one or more trackable portions (e.g., reflective spheres) that are associated with the tracking device or array 40. The trackable portions may be viewed by the cameras 54 and a signal may be transmitted to a navigation processor unit 70. The navigation processor unit 70 may include various features, such as a navigation probe interface (NPI), as discussed further herein. The navigation processor unit 70 may also include a coil array controller (CAC) for various types of tracking systems. Various features such as the NPI, the CAC, or other portions may be provided as separate units from the navigation processor unit 70 or separate modules for interacting with various portions of the navigation system, as is generally known in the art.

The localizer 50 may communicate with the navigation processor unit 70 via a selected communication line 74. The communication line 74 may be a wired or a wireless communication with the navigation processor unit 70. The navigation processor unit 70 may communicate with a selected system, such as a workstation, a terminal, or the like that includes a display system or display module 80 having a display screen 84 and one or more user inputs 88. It is understood, however, that the display screen 84 may be separated for the processor unit 70 and/or in addition thereto, such as a projected display, a headset display (e.g., augmented reality systems). The user inputs 88 may include a keyboard, a mouse, a touch screen, or other tactical input. Further inputs may also include a foot switch, verbal inputs, visual inputs, or the like.

A subject tracking device 98 may also be connected, such as fixed, relative to the subject 28. In various embodiments, the subject tracking device 98 may be fixed to one or more of the vertebra 36 and/or other portion of the subject 28. Generally, the subject tracking device 98 is fixed relative to a selected portion of the subject 28. In various embodiments, for example, the subject may be positioned on and/or fixed to a subject support 90 to which the subject 28 is fixed, at least for a selected period.

In various embodiments, alternative or additional tracking systems may be provided, such as an electromagnetic tracking systems including an electromagnetic tracking array, such as a coil array 100. The coil array 100 may include one or more coil elements 104 that emit and/or receive an electromagnetic signal from an electromagnetic (EM) tracking devices, such as a subject tracking device 98' associated and/or connected to the patient 28 or a tracking device 40' connected to the instrument 20. The coil array 100 may communicate with navigation processing unit 70 via a communication line 110 similar to and/or the same as the communication line 74 from the localizer device 50 to the navigation processing unit 70. Further, each of the tracking devices may communicate with the navigation processing unit 70 via selected communication lines such as communication line 114 so that a position of the selected tracking devices, including tracking device 40 and tracking device 98 may be determined with a navigation processing unit 70. It is understood that one or more than one tracking system may be used simultaneously and/or serially during the selected procedure.

The display screen 84 may display an image 120 of a portion of the subject 28, such as a vertebra image 36i of the vertebra 36. The image 120 may be based on or generated with image data acquired with the imaging system 10 as discussed above. Displayed relative to the image 120 and/or superimposed on the image 120 of the patient 28 may be a graphical representation, also referred to as an icon, 124. The icon 124 may represent position and/or orientation, also referred to as a pose, of the instrument 20 relative to the subject 28. The represented position may also be of only a portion of the assembly 20. The position of the powered drill assembly 20, or a portion thereof, relative to the subject 28 may be determined by registering the powered drill assembly 20 relative to the subject 28 and thereafter tracking the location of the powered drill assembly 20 relative to the subject 28.

The tracking and display of the instrument 20 relative to the image 120 of the subject 28 may be due to registration of an image space of the image 120 to a subject space of the subject 28. Registration may include various techniques, such as those disclosed in U.S. Pat. Nos. RE44,305; 7,697,972; 8,644,907; 8,238,631; and 8,842,893; and U.S. Pat. App. Pub. No. 2004/0199072, all incorporated herein by reference. Generally, registration includes a mapping between the subject space and the image space. This may be done by identifying points in the subject space (i.e. fiducial portions) and identifying the same points in the image (i.e. image fiducials). A map of the image space to the subject space may then be made, such as by the navigation system. For example, points may be identified manually, automatically, or a combination thereof in the image data, such as in the image 120.

Related points may be identified in a subject space, such as defined by the subject 28. For example, the user 24 may identify a spinous process in the image 120 and an instrument tracked by one or more of the tracking systems, including the localizers 50, 100, may be used to identify a spinous process at the vertebrae 36. Once an appropriate number of points are identified in both the image space of the image 120 and the subject space of the subject 28, a map may be made between the two spaces. The map allows for a registration between the subject space defined by the subject, also referred to as a navigation space, and the image space defined by the image 120. Therefore, the instrument, or any appropriate portion, may be tracked with a selected tracking system and a poise of the instrument may be identified or represented relative to the image 120 with the graphical representation 124.

As discussed above, registration of the instrument 20 relative to the subject 28, such as with or to the subject tracking device 98, may be made at a selected point in a procedure. The image 120 may then be displayed on the display screen 84 and a tracked location of the powered drill assembly 20 may be displayed as the icon 124 relative to the image 120. The icon 124 may be superimposed on the image 120 to display a pose of at least a selected portion of the instrument 20. As briefly noted above, the pose or position may include a location that includes three degrees of freedom in space (for example, including at least one of a XYZ position) and a selected number (e.g., three) degrees of freedom orientation information location (for example, including at least one of yaw, pitch and roll orientation). The pose may be determined and/or calculated by the navigation processing unit 70 and communicated to the display device 80 via a selected communication line, such as a communication line 130. The communication line 130 may be a wired or wireless or other appropriate communication line.

Further, it is understood that the navigation processor unit 70 may include various features such as a selected processor (e.g., an application specific integrated circuit (ASIC), general purpose processor or the like). The navigation processor unit 70 may also include a memory system (e.g., non-transitory memory systems including spinning hard disks, non-volatile solid state memory, etc.) that includes selected instructions, such as those to perform the tracking, registration, superimposing of the icon 124 on the image 120, or the like. Therefore, the determined pose of the instrument 20 (for example the selected portion of the instrument 20, as discussed further herein), may be displayed relative to the subject 28 by the icon 124 relative to the image 120. The user 24 may then be able to view the display screen 84 to view and/or comprehend the specific pose of the selected portion of the instrument 20 relative to the subject 28 by viewing the display 84.

Figure 2A:
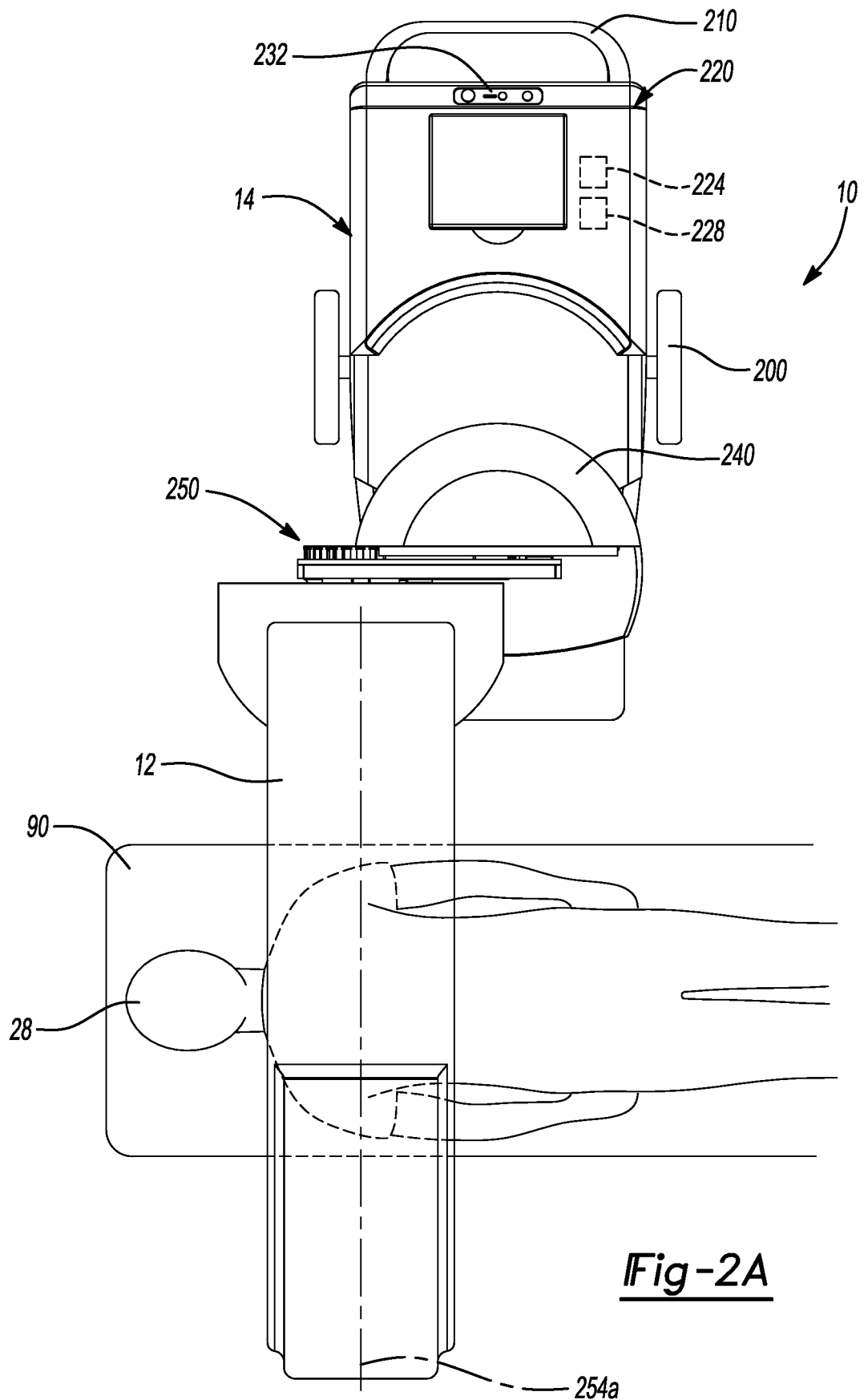
FIG. 2A is a top view of an imaging system with a gantry in a first position, according to various embodiments.
Figure 2B:
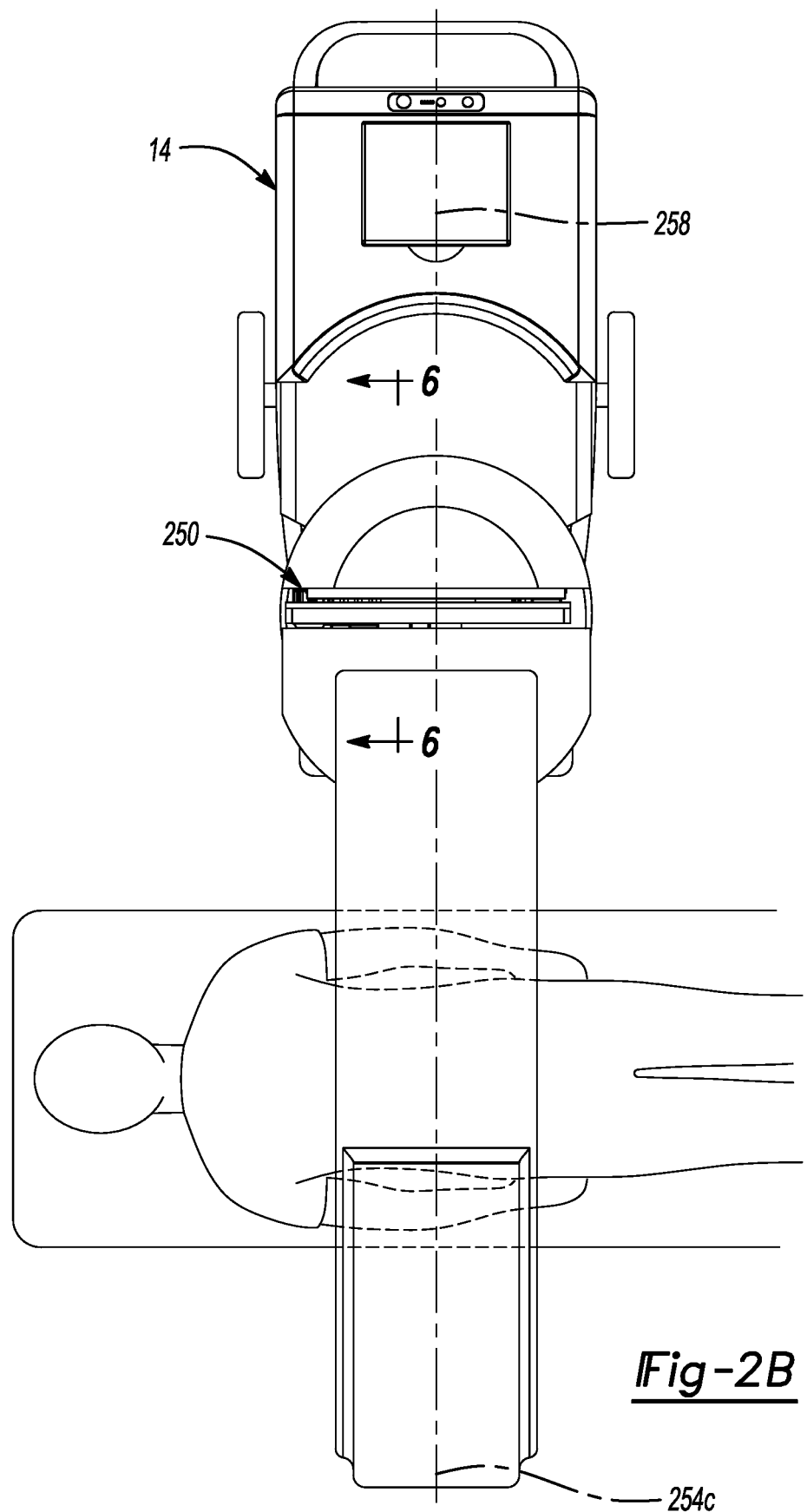
FIG. 2B is a top view of an imaging system with a gantry in a second position, according to various embodiments.
Figure 2C:
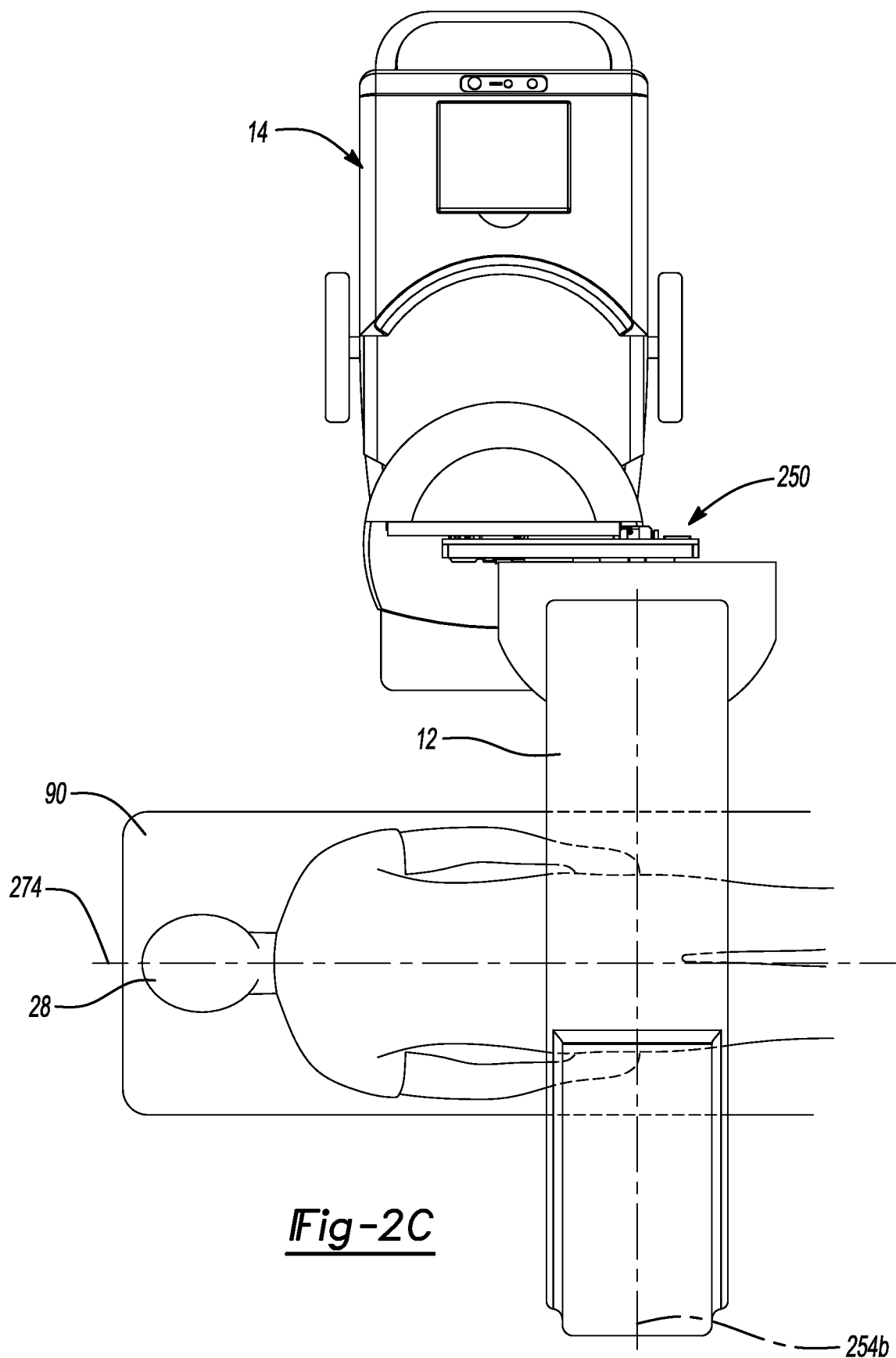
FIG. 2C is a top view of an imaging system with a gantry in a third position, according to various embodiments.

With continuing reference to FIG. 1 and additional reference to FIGS. 2A-2C, the imaging system 10 includes the gantry 12 and the mobile base or cart 14. The mobile base or cart 14 may move relative to the subject 28 and/or the subject support 90 by movement of a mobile portion, such as a wheel 200. The wheel 200 may be operated (e.g., powered) and/or pushed to move the mobile base 14 relative to the subject 28 and/or the support 90. In various embodiments, for example, the mobile base 14 may be moved from one operating theater to another to image a plurality of patients. Further, the imaging system 10 may be moved from near or adjacent to the subject 28 to a location away from the subject 28 for a selected periods of a procedure. For example, image data may be acquired of the subject 28 prior to or initially during a procedure and then the imaging system 10 may be moved away from the subject 28 while performing at least a portion of the procedure. The imaging system 10 may then be repositioned relative to the subject 28 to acquire additional image data.

The mobile base 14 may further house or include various portions, such as a control handle or mechanism 210 and allow a user to move the mobile base 14. The mobile base 14 may include one or more control systems 220 which may include a control processor 224, an imaging processor 228 or other appropriate portions. Inputs (e.g. selections) may be made with user inputs 232 to allow for operation of the imaging system 10, movement of the imaging system 10, or other appropriate portions. Regardless, the control processor may be operated or execute instructions to control movement of at least the gantry 12 relative to the subject 28 and the imaging processor 228 may be used to acquire and/or analyze image data acquired with the imaging system 10. Further the imaging processor 228 may execute instructions to generate images, such as the image 120, with image data acquired with the imaging system 10. The imaging system 10 may communicate with the navigation processor 70 with the communication line 234 to transmit image data from the imaging system 10 to the navigation processor 70 to assist in navigation, such as image guided surgery, as noted above. It is understood that the communication line 234 may be a wired communication line, wireless communication line, or any other appropriate communication.

Further the mobile base 14 may include a support portion 240. The support portion 240 may support the gantry 12 relative to the subject 28 and allow movement and support movement of the gantry 12 relative to the subject 28.

Movement of the gantry 12 relative to the subject 28 may be with a telescoping or gantry movement assembly 250. The gantry movement assembly 250 may allow movement of the gantry 12, as discussed further herein. In various embodiments, the gantry 12 may move relative to the subject from a first or initial terminal position relative to the subject 28, as illustrated in FIG. 2A to a final terminal position, as illustrated in FIG. 2C relative to the subject 28. The movement of the gantry 12 may be defined relative to any appropriate portion of the gantry 12, such as relative to a central line or axis 254. As illustrated in FIG. 2A, the central axis 254 may be in an initial position 254a while the central axis 254 may be in a final position 254b in FIG. 2C. The gantry 12 may move through other positions, such as a mid-position where the central axis 254 of the gantry may be in a mid-position 254c that may be aligned with an axis 258 defined through the mobile base 14.

The distance between the initial position 254a and the final position 254b may be achieved without movement of the mobile base 14 relative to the subject 28. Therefore, the gantry 12 may move relative to the subject 28 due to the movement of the telescoping assembly 250, as discussed further herein. The movement distance between the initial position 254a and the final position 254b may be an appropriate distanced such as about 50 cm to about 80 cm, including about 60 cm to about 70 cm, and further including at least about 62 cm. Accordingly, the gantry 12 may move relative to the mobile base at least at about 62 cm from the initial position 254a to the final position 254b. This movement of the gantry may also be movement relative to the subject 28 as illustrated in FIGS. 2A-2C.

The gantry 12 may move relative to the subject 28. At various selected positions at and/or between the initial position 254a and the final position 254b image data may be acquired of the subject 28. Further, the gantry 12 may move continuously from the initial position 254a to the final position 254b and image data may be acquired while moving at any selected position and/or at the entire or during the entire time of movement.

Image data may be acquired of the subject 28 with an appropriate imaging system, such as an x-ray imaging system. The imaging system 10 may include an emitter 260 and a detector 264. The emitter 260 may emit x-rays that may travel through the subject 28 and/or be attenuated by the subject 28. X-rays that travel through the subject 28 may be detected at the detector 264. The detected x-rays may be used to generate images of the subject 28, such as the image 120. The emitter 260 may emit the x-rays in an appropriate manner, such as in a cone beam for generation of the image data with the imaging system for generating the image 120.

The imaging system 10, including the emitter 260 and the detector 264, may generate an image with image data acquired due to and/or during movement of the gantry 12. The image data may be acquired to generate an image, such as the image 120, of the subject 28 that may have a length or dimension along an axis 270 that may be equivalent to or based upon an axis 274 of the subject 28. The dimension or extent of the image 120 along the axis 270 may generate an image that includes about 50 cm to about 150 cm, including about 90 cm to about 95 cm, and further including about 70 cm to 93 cm along the axis 270. In various embodiments, the image 120 may include an image of a length of at least about 70 cm to at least about 90 cm along the axis 270.

The image 120 generated with movement of the gantry 12 from the initial position 254a to the final position 254b may be used for performing a procedure on the subject 28. The gantry, however, may move relative to the mobile base 14 to acquire the image data of the subject 28 without requiring movement of the mobile base 14. Thus, the mobile base 14 may be fixed or held in a single position while the gantry 12 moves relative to the subject 28 to acquire the image data. The gantry 12 may be moved or operated to allow positioning of the patient support 90 within a gantry 12 prior to movement of the gantry 12.

A gantry tracking device 280 may be positioned on the gantry 12 to track motion or movement of the gantry 12, such as during acquisition of the image data, and determine the pose of the gantry 12 during image data acquisition. The gantry tracker 280 may allow for tracking a position of the gantry 12 which may be related to the subject 28, such as due to the subject tracker 98. The gantry tracker 280 may be tracked in any appropriate manner and, therefore, registered to the patient tracker 98, as discussed above. Due to tracking the gantry 12, such as with the gantry tracker 280, image data acquired of the subject 28 may be automatically registered to the subject 28 due to the registered or correlated tracked position of the gantry 12 and the subject 28 during the acquisition of the image data. Alternatively, movement of the gantry and/or position of the gantry 12 may be determined due to movement of the telescoping system 250 as discussed herein. The image 120 may be automatically registered to the subject 28 without further registration procedures.

With continuing reference to FIGS. 1-2C, the telescoping assembly 250 is mounted or positioned between the gantry 12 and the support 240 of the mobile base 14. The telescoping or translating assembly 250, with initial reference to FIG. 3, may include a first or fixed rail or rail portions 300. The fixed rail portions 300 may be fixed to the support portion 240. A second or movable rail portions 304 may be movably positioned and assembled to the first or fixed rail portions 300. A gantry mounting member 310 may mount to the gantry 12 and also be movable relative to the second rail assembly 304 and/or the first rail assembly 300.

Movement of the second rail portion 304 and the gantry mount 310 may be driven by a selected drive assembly 314. The drive assembly 314 may include a motor 318 that drives a drive gear 322 that, in turn, drives a belt 326. The belt 326 may include belt teeth that engage gear teeth on the drive gear 322. The belt 326, therefore, may be moved when the drive gear 322 is moved, such as rotated, when driven by the motor 318. The belt 326 may be coupled to the gantry mount 310 and/or other selected portion such as a frame portion 404, such as through a coupling member 340. The belt 326 may be further fixed or anchored relative to the support portion 240 and/or the fixed rails 300 with a second mount 344. It is understood by one skilled in the art that the belt 326 may be a driven member that may be in addition or alternative to a belt such as a chain, a rack and pinion system, or other appropriate motive system that is driven by the motor 318.

Figure 3:
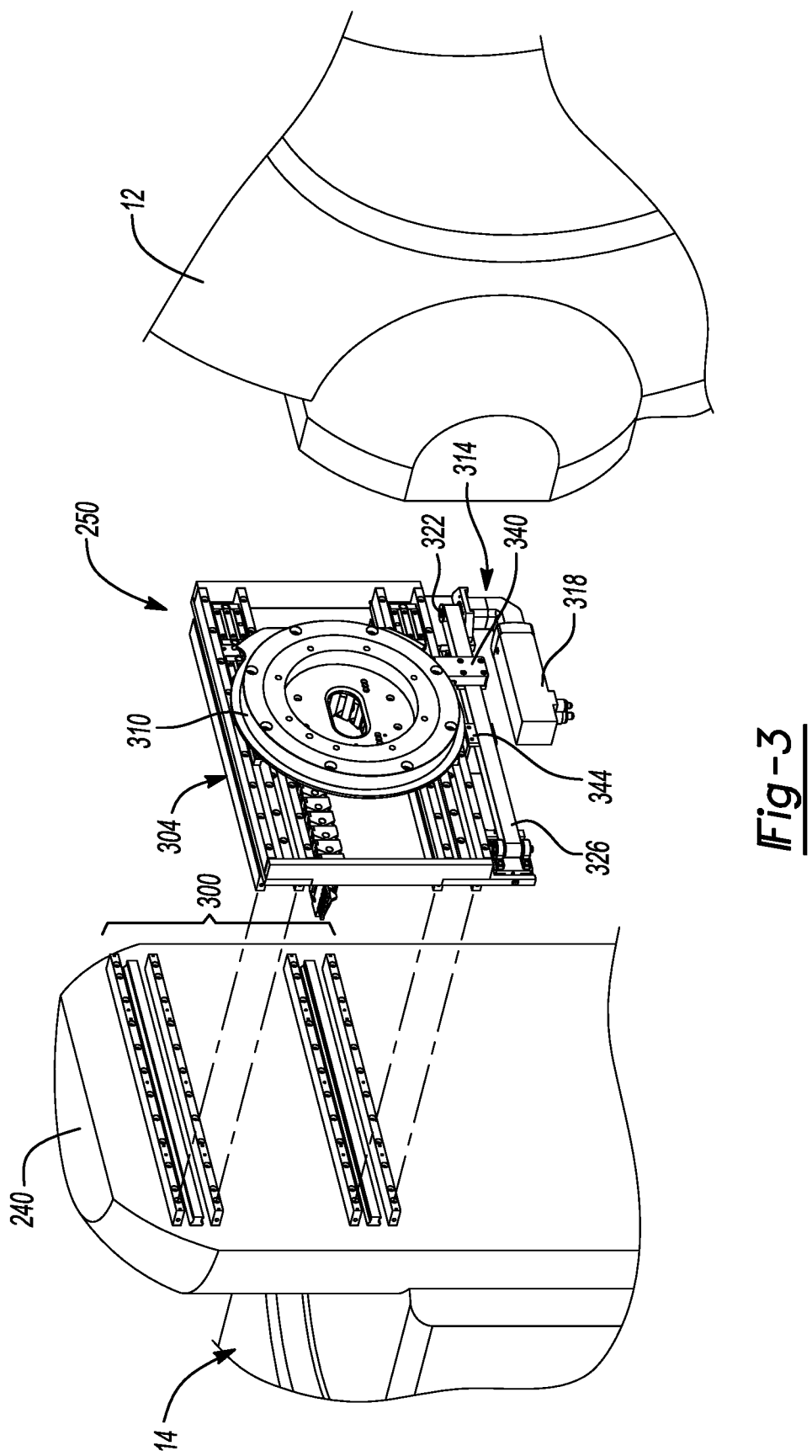
FIG. 3 is a detail exploded view of an imaging system, according to various embodiments.

With continuing reference to FIG. 3 and further reference to FIGS. 4, 5, 6, and 7, the gantry movement or telescoping assembly will be discussed in further detail.

The telescoping assembly 250, as noted above, generally includes the fixed portion 300 that is fixed to the support portion 240 of the movable base 14. The fixed portion 300 generally includes one or more rail members 388, 392 and one or more auxiliary bars or members 360, 364, 368, and 372 that may also be referred to as support members. In various embodiments, the auxiliary members 360, 364, 368, and 372 may operate or be configured to be guards to prevent anything from getting in the way of the carriages and/or provides surfaces for cover attachment. It is understood by one skilled in the art that the auxiliary members 360, 364, 368, and 372 are not critical or necessary to operation of the telescoping assembly 250 and/or movement of the gantry.

Figure 4:
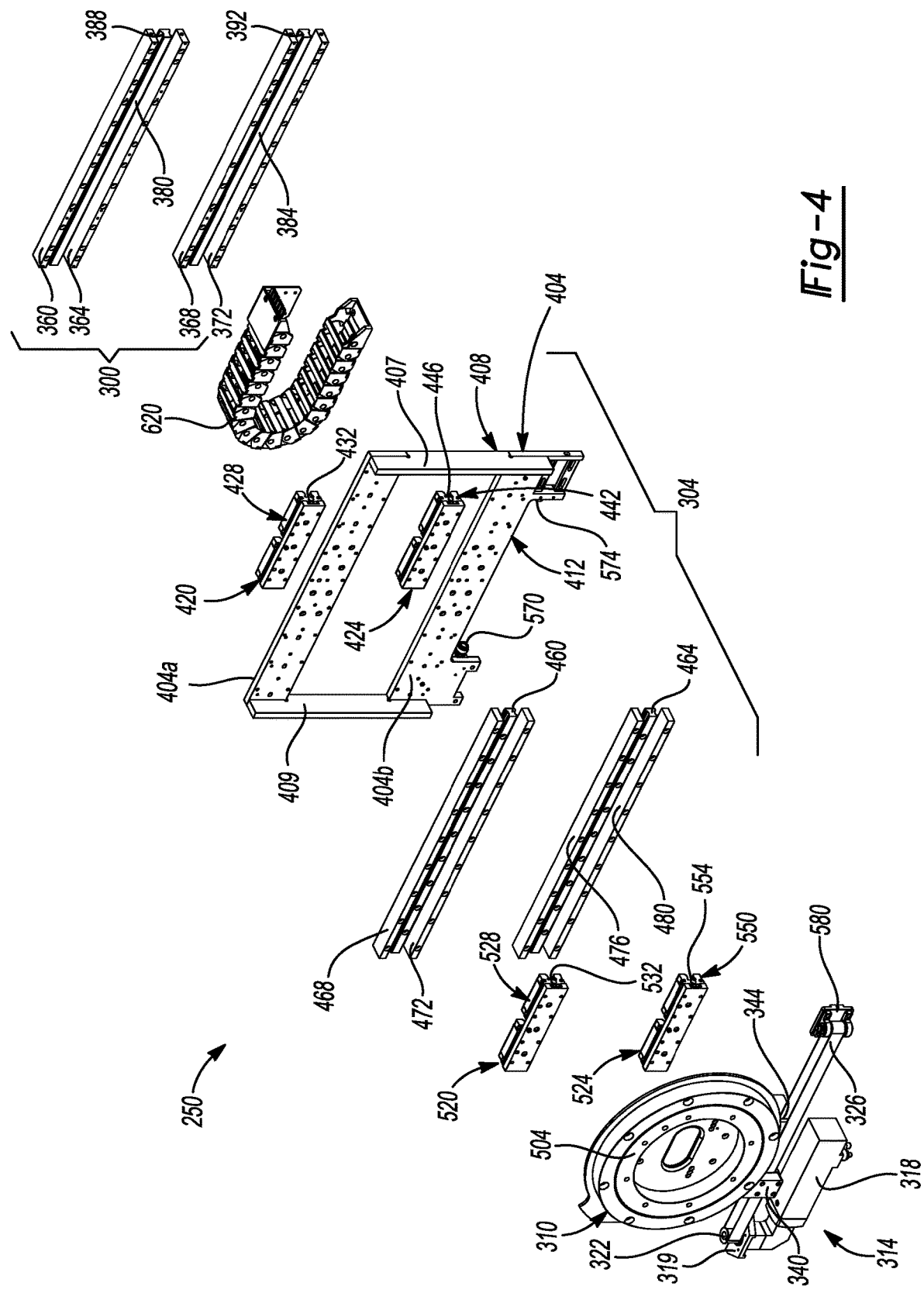
FIG. 4 is a detail exploded view of a telescoping drive mechanism from a first perspective, according to various embodiments.
Figure 5:
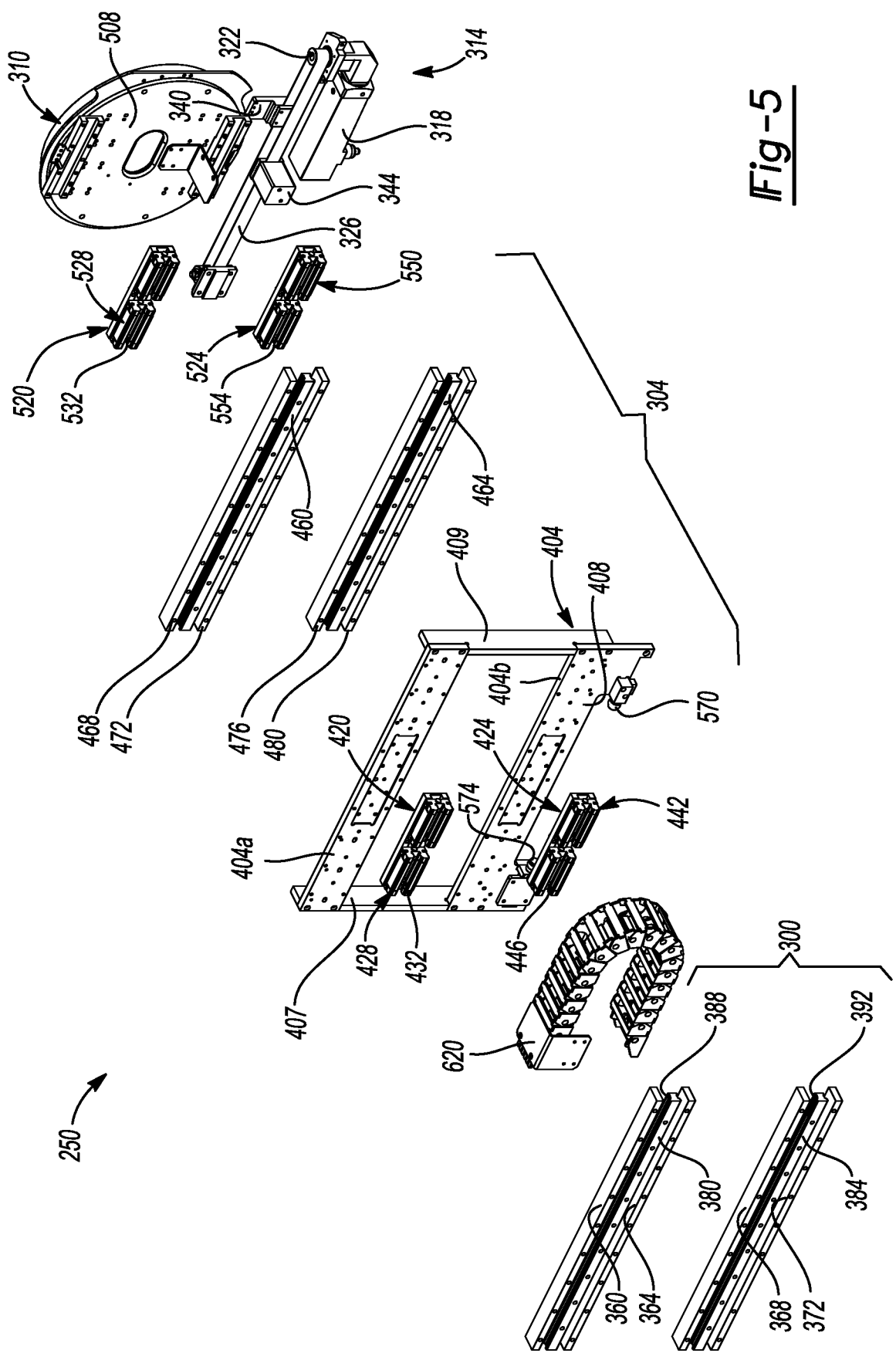
FIG. 5 is a detail exploded view of a telescoping drive mechanism from a second perspective, according to various embodiments.
Figure 6:
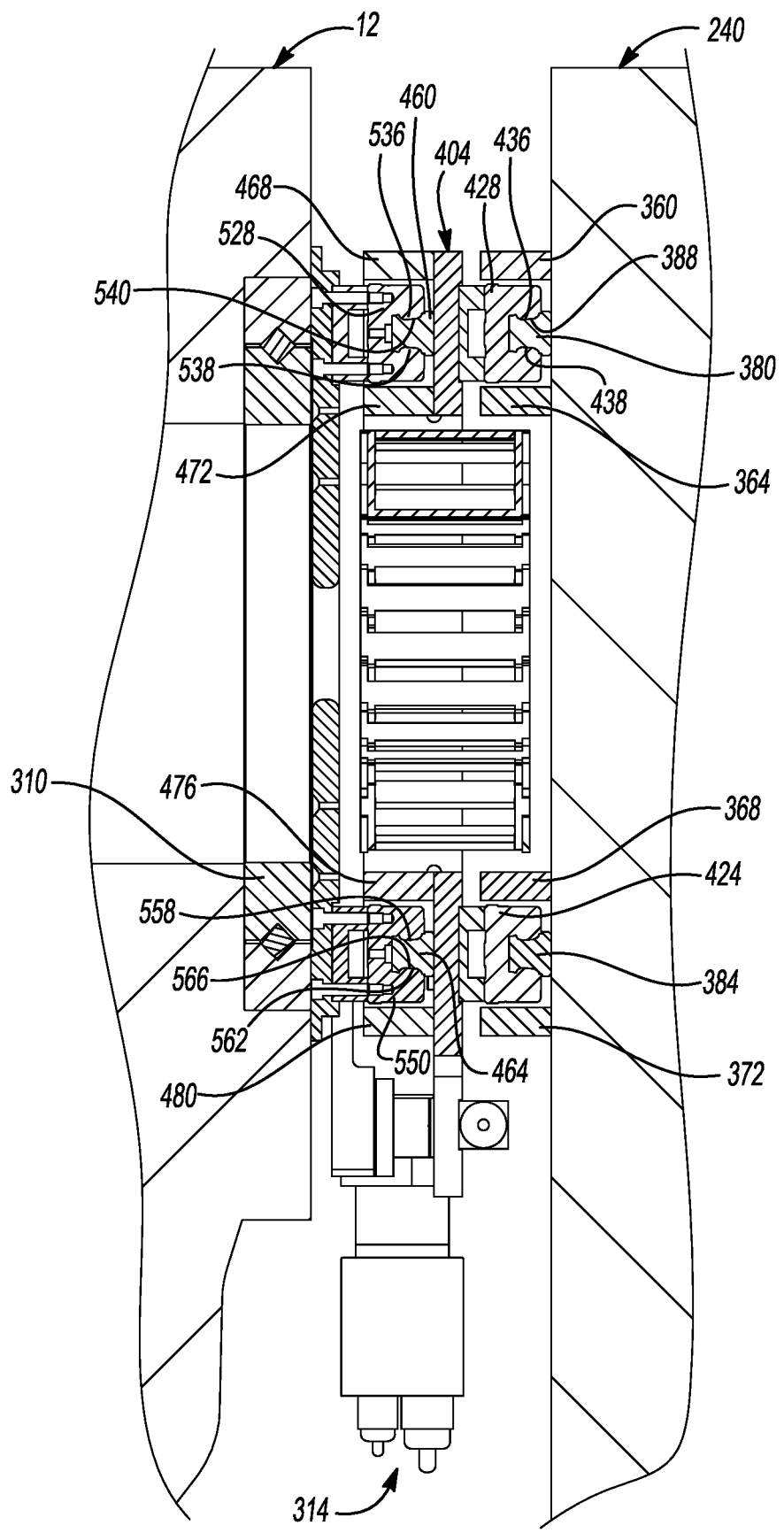
FIG. 6 is a detail cross-section view taken along line 6-6 of FIG. 2B.

As illustrated in FIGS. 4 and 5, the fixed portion 300 may include four auxiliary member 360, 364, 368, and 372. Two auxiliary members 360, 364 may be positioned on either side of a first track member 380 and the two auxiliary members 368, 372 may be positioned on either side of a second track member 384. Each of the track members may include grooves or lands 388, 392, respectively. The lands or grooves 388, 392 may engage with a mount or riding portion, as discussed further herein. As the rails 388, 392 are fixed to the support portion 240, a moving portion may move relative to the fixed portion 300. The rails 388, 392 may be provided as two rails and/or any appropriate number of rails. The rails may be formed of appropriate materials such as such as metal or metal alloys or other appropriate materials that are formed to include a selected rigidity and strength to carry the gantry 12. For example, the MH series rails sold by IKO International, having a place of business at Parsippany, NJ and/or the 500 Series rails sold by Thomson Industries, Inc. having a place of business at Radford, VA Further, the auxiliary members 360-372 may be provided in the appropriate number, such as two auxiliary members per rail and any appropriate number. Nevertheless the fixed portion 300 allows for other portions of the telescoping assembly 250 to move relative to the fixed portion 300.

In various embodiments, the intermediate or second rail assembly 304 is provided. The intermediate rails assembly includes a frame member or support member 404 that includes a support facing side 408 and a gantry facing side 412. The support frame 404, and the support portion facing side 408, may engage or have mounted thereon one or more cars or rail riding members, such as a first rail riding member 420, and a second rail riding member 424. Each of the rail riding members may include similar portions, such as rail engaging members or assembly 428. The rail engaging assemblies 428 may form or define a groove or slot 432 to engage or receive the rail, such as the rail 388. Each of the rail engaging portions 428 may include a detent or projection, such as a projection 436. In various embodiments, the rail riding portion 428 may include two projections, such as a second projection 438. Further the rail riding portion 428 may generally define a C-shape or a U-shape to engage two edges or grooves of the rail member 380.

Similarly, the second rail engaging or riding member 424 can include a rail engaging portion 442 that defines one or more slots or grooves 446. Within the groove 446, the second rail 384 may similarly by engaged. Also, the second rail engaging portion 424 may form or define a C or U-shape to engage and surround the rail member 384. The rail engaging portion 424 may further include projections, similar to those discussed above, to engage the rail member 384. The rail engaging portions may also be referred to as carriages and may include those with appropriate strength and characteristics to carry the gantry 12. For example, the carriages included and/or for use with the MH series rails sold by IKO International, having a place of business at Parsippany, NJ and/or the 500 Series rails sold by Thomson Industries, Inc. having a place of business at Radford, VA may be appropriate.

Accordingly, the frame member 404 may include or have mounted thereon at least two rail riding portions 420, 424. These rail riding portions may engage the respective rails 380, 384 to allow for movement of the frame 404 relative to the rails 380, 384. As discussed further herein, therefore, the frame member 404 may move relative to the frame assembly 300. It is further understood that any appropriate number of rail riding members may be provided such as splitting or including rail riding members on a top or upper portion 404a of the frame and two rail riding portions on a bottom riding portion 404b of the frame. Thus, the moving section 304 may include any appropriate number of rail engaging portions to engage the rails 380, 384. Moreover, as discussed above, the fixed portion 300 may include any appropriate number of rail members that are mounted or fixed to the support assembly 240 and therefore the frame member 404 may include an appropriate number of rail engage members to engage the rails as is understood by one skilled in the art.

On the gantry facing side 404b of the frame 404 may be a second set or a second track portion, including a third track 460 and a fourth track 464. The third and fourth tracks 460, 464 may be substantially similar to the first tracks 380, 384. It is understood, however, that the third and fourth tracks, 460, 464 may also be designed in any appropriate manner. Similarly each of the tracks 460, 464 may have one or more associated auxiliary members, such as a fifth auxiliary member 468, and a sixth auxiliary members 472 for the third rail member 460. Similarly a seventh auxiliary member 476 and an eighth auxiliary member 480 may be provided relative to the fourth rail member 464. The auxiliary members 468-480 may operate similar to the auxiliary members as discussed above.

The third and fourth rail members 460, 464 may be mounted to the gantry side 12 of the frame assembly 404. For example, the third rail member 460 may be mounted to the top or first frame portion 404a while the fourth rail member 464 is mounted to the bottom portion 404b. Therefore, the third and fourth rail members 460, 464 may be fixed relative to the frame member 404. In this manner, while the frame member 404 may move, the rail members 460, 464 will not move relative to the frame member 404. The rails 460, 464, however, may move with the frame member 404, such as relative to the fixed rail portion 300. Movement of the frame assembly 404, and the associated rails 460, 464, will be discussed in further detail herein.

The gantry mount member or portion 310 may be fixed to the gantry 12 in any appropriate manner. For example, one or more bolts, screws, or the like fasteners may be used to assemble the gantry mount member 310 to the gantry 12. Other fixation mechanisms may also be provided such as welding, adhesives, or the like. Nevertheless, the gantry mount 310 may be fixed to the gantry 12 such that the gantry mount 310 does not substantially move relative to the gantry 12 once assembled.

The gantry mount 310 may include a gantry facing portion or surface 504. The gantry mount 310 may also include a support facing portion or face 508. Mounted to the support facing face or face 508 may also be one or more rail riding or car portions such as a first rail riding portion 520 and a second rail riding portion 524. The rail riding portions 520, 524 may be similar to the first and second rail riding portions 420, 424 discussed above. Accordingly, the third rail riding portions 520 may include a rail engaging portion 528 that includes or defines a groove or slot 532. The groove or slot may include one or more projections, such as a first projection 536 and a second groove or projection 538. The projections 536, 538 may engage respective grooves 540 of the rail, similar to those discussed above. Further, the rail engaging portion 528 may generally define a C or U-shape to engage at least two sides of the rail member 460. The second rail engaging portion 524 may also include a rail engaging portion or member 550 that defines or forms a groove 554. Similarly, the rail 480 may be positioned within the slot or groove 554. The rail engaging portion 550 may further include two projections 558 and 562 to engage respective grooves or a groove 566 of the rail 480. Further, the rail engaging portion 550 may generally define or be shaped as a "C"- or a "U"-shape to engage at least two portions of the rail 464.

Accordingly, the rail engaging portions 520, 524 may be fixed to the gantry mount plate 310, such as on the support face 508. The rail engaging portions may then be formed or provided the respective rails 460, 464 that are fixed to the frame 404. The rail engaging portions 520, 524 that are fixed to the gantry mount 310 allow for movement of the gantry mount 310 relative to the rail 460, 464. As the rails 460, 464 fixed to the frame 404, therefore, the gantry mount 310 may also move relative to the frame 404. This allows the gantry mount 310 to move relative to the frame 404 and relative to the fixed rail portions 300, as discussed further herein. As also discussed further herein, the gantry mount 310 is fixed to the gantry 12 and, therefore, the gantry 12 also moves relative to the frame 404 and the fixed rail members 300.

The telescoping assembly 250 is driven or moved by the drive assembly 314, as noted above. The drive assembly 314 includes the motor 318. The motor 318 can be an appropriate motor to move the gantry 12 at a selected speed and/or distance. Various motors may include Baldor® electric motors sold by ABB Motors and Mechanical, Inc. having a place of business at Fort Smith, AR including the BSM N-series brushless servo motors that may been selected to have appropriate torque and force generation and/or operate with an appropriate gearbox. It is understood, however, that the motor 318 may be any appropriate powered drive system such as a pneumatic, electric, and/or combinations thereof, etc. The motor 318 may be mounted relative to the frame 404, the gantry 12 and/or the support portion 240. Therefore, the motor 318 may be held relative to the drive gear 322. The drive gear 322 may be driven by the motor 318 when operated or commanded to do so. As discussed above, the imaging system 10 includes the imaging control system or processor 224. The imaging and control processor 224 may execute instructions to operate the motor 318 to move the gantry 12 relative to the mobile base 14.

The motor 318 may be controlled and include various sensors such as speed sensors, position sensors, and the like. The motor 318, therefore, may be provided as a feedback motor to ensure a selected position and/or a speed of movement of the gantry 12. As discussed above, image data may be acquired of the subject 28 by movement of the gantry 12 and a selected image data quality, type, or the like may be acquired by selected movement of the gantry relative to the subject 28. It is further understood that various position sensors may be provided at or by the support portion 240 and/or the gantry 12 to determine or measure a position and/or amount of movement and/or speed of movement of the gantry 12 relative to the support portion 240. Position sensors may also and/or in addition be located on the motor 318. Sensors (e.g., linear sensors) could be located on the rail portions 300, 304 as an alternative or additional sensor location.

As noted above, the drive assembly 314 may include the drive belt 326. The drive belt 326 may be fixed to the belt fixing portion 340 that is fixed to the gantry mount 310. The gantry mount 310 may ride on the rails 460, 464 due to the rail engaging portions 520, 524, as discussed above. The drive belt 326 may apply a force to the belt mounting portion 340. Therefore, movement of the belt 326, such as being driven by the motor 318, may cause the gantry mount 310 to move along the rails 460, 464. The belt 326 may also be fixed to a support mount 344. The support mount 344 may be fixed relative to the support portion 240. Further selected tensioning or idling portions, such as an idling pinion 580 may be provided to ensure an appropriate positioning and/or tension of the belt 326 for use of the imaging system 10.

Movement of the belt 326, while anchored at the support portion support or mount 344, causes the gantry mount 310 to move and also the frame 404, such as when the gantry mount 310 reaches or is stopped on the frame 404. For example, the frame 404 may include or have extending therefrom a first stop 570 and a second stop 574. The stops 570, 574 may be engaged by the drive connection portions 340, 344. These may be used to home the drive system, but are not required. The Frame 404 may further include side members 407, 409 to assist in forming the frame. Accordingly, the telescoping or moving portion 250, as discussed above, may be used to move the gantry 12 from and/or between the initial position 254a to the final position 254b (which may also be referred to as a first to second position) and/or selected locations therebetween.

A cable guard 620 may be used to route and guard a cable that extends between the movable base 14 and the respective controls and processors therein and the gantry 12, including the respective emitters, detectors and the like. The cable guard 620 may be mounted or provide an access port at a fixed point or portion 623 relative to the support portion 240. The point 623 may be a center point and/or on a center line 624 regarding relative movement, as discussed herein, and or selected position relative to the system 10.

Figure 7:
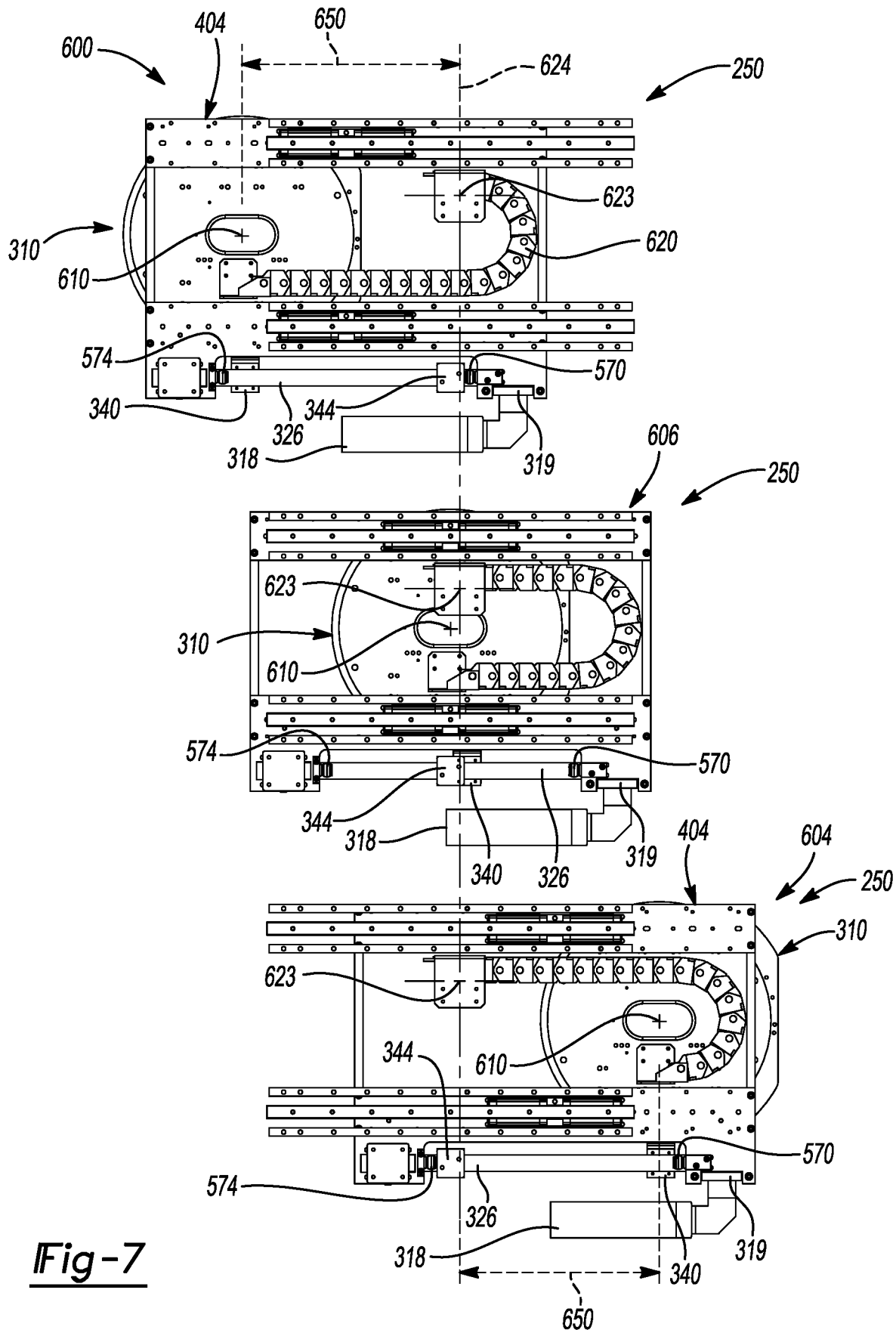
FIG. 7 is a detail view of the telescoping drive in three positions.

With continuing reference to FIGS. 1-6 and additional reference to FIG. 7, the moving assembly 250 is illustrated in three positions, such as in the first or initial position equivalent to initial position 254a illustrated as initial position 600 in FIG. 7, a final position 604 equivalent to the final position 254b discussed above, and an intermediate position 606 equivalent of the intermediate position 254c as discussed above. In each position, the gantry mount 310 may have a center point or point 610 that is on or defined by the axis 254 as discussed above. As the motor 318 is operated to drive the drive belt 326, the belt 326 is anchored at the support portion mount or anchor 344 which causes the belt 326 to move or drive the gantry belt mount 340 to move the gantry mount 310 to the respective positions 600, 604, 606.

Illustrated in FIG. 7 is an exemplary movement/motion of the gantry mount 310, to which the gantry is attached. In a selected position, also referred to as the initial position, 600, the center point 610 of the gantry mount 310 is positioned at a first extreme or extent relative to a point or position 624, such as the point 624 which may be a center of the rail portions 300,304 and/or a point relative to the anchor 344. The gantry mount 310 has moved a selected amount and/or the stop 574 has been engaged. As the frame 404 is attached to the belt 326, such as via the motor mount/drive 319 and/or the mount 340, the frame 404 has also moved along with the gantry mount 310 to allow the gantry mount 310 to reach the initial extent 600. The gantry mount 310 may be moved to the second extent or position, also referred to as the final position, 604 such that the center point 610 is at a second extent or maximum distance from a selected point, such as the center point 624. As illustrated in FIG. 7, the gantry mount 310 may be moved a selected amount (and in various embodiments engage the stop 570) and the frame 404 may also move in combination with the gantry mount 310.

Thus, the portion 250, including the gantry mount 310 and the frame 404 moves in concert with the motor 318 and due to the drive of the motor 318 move between (i.e., any selected position between) the initial position 600 and the final position 604. The telescoping motion is driven, in various embodiments, entirely by the belt 326 powered by the motor 318. As illustrated, one side of the belt 326 is anchored at the member 344 to the support 240 portion. When driven, the frame 404 is moved the length of the belt 326 and the movable rail portions 304 move with the frame 404. At the same time, the anchor portion 340 on the other side of the belt 326 causes the gantry mount 310 to move at the same speed relative to the movable rail portions 304. The gantry mount 310 (and the related gantry 12) is carried by the center stage movable rail portions 304 and also travels relative to the center stage movable rail portions 304 as all portions are being driven by the belt 326. As noted above, however, the belt driven system is merely exemplary and other drive systems may be used, such as a rack and pinion system.

Further, the gantry mount 310 is able to move to any position between the two extents or extremes, including the initial position 600 and the final position 604. For example, the mount 340 may be driven by the motor 318 due to the belt 326 to the intermediate position 606. The gantry mount 310 may move in a continuous (e.g., smooth or selected motion) from the initial position 600 to the final position 604 and/or back. Therefore, the gantry 12 which is mounted to the gantry mount 310 may move to any appropriate position or selected position between the initial position 600 and final position 604.

The gantry 12 is supported relative to the support portion by the telescoping assembly 250. The assembly 250 allows the gantry support 310 that is connected to the gantry 12 to move relative to the central portion a selected distance, such as a distance 650. The distance 650 may be a selected distance such as about 28 cm to about 35 cm, including about 30 cm to about 33 cm, and further including at least about 31 cm. The gantry mount 310, mounted to the gantry 12, may also move in a second or opposite direction from the center a second distance 650' that may be substantially equal to the first distance 650.

As illustrated in FIG. 7, the telescoping assembly 250 may be positioned such that the frame 404 has traveled the distance along the fixed track portion 300 and the gantry mount 310 has also traveled a distance along the frame 404. Therefore, the frame 404 may move relative to the fixed track portion 300 a selected distance such as 10 cm to about 35 cm, including about 10 cm to about 34 cm. In various embodiments, the distanced traveled may be about one half a total distance and include about 8 cm to about 20 cm, including about 17 cm. As discussed above, in various embodiments, the gantry mount 310 may move a distance relative to the frame 404 and the frame 404 may move relative to the fixed portion 300. Therefore, the gantry mount portion 310 may move a distance relative to the central line 624 a greater distance due to the inclusion of the frame member 404.

In a selected operation, therefore, the user may select to acquire image data of the subject at a position or over a length that may be provided between the initial position 254a and the final position 254b. The user may operate or command the imaging system 10 to acquire the selected image data. The imaging system 10 may then determine the amount of movement and/or position of the gantry 12 to acquire the image data. The gantry 12 may, therefore, be moved to achieve acquisition of the selected image data to generate a selected image. This allows image data to be acquired of the subject 28 at and/or between the two extent positions. Further, the user 20 may select a position for acquisition of image data and the gantry 12 may be moved thereto between and/or at any of the points at or between the initial position 254a and the final position 254b. It is further understood, image data may be collected while the gantry 12 is in motion between any two or more selected points. Thus, the gantry 12 need not be stopped at any one selected point to and/or while acquiring image data.

As noted above, the gantry 12 may be moved to acquire image data of the subject 28. The gantry 12 may be affixed to the telescoping assembly 250 as discussed above to allow movement of the gantry 12 relative to the subject 28 and the mobile base 14. The telescoping assembly 250, as illustrated in FIGS. 2A-2C, may be interconnected between the gantry 12 and the support portion 240. With reference to FIG. 8, in addition thereto and/alternatively thereto, a telescoping and/or movement assembly 700 may be included in an imaging system 10'.

The imaging system 10' may include various portions similar or identical to those discussed above and will be referenced here with a prime (') identical to those above unless otherwise indicated. The imaging system 10' may include a gantry 12', a mobile cart 14', and a support portion 240'. As discussed above, the gantry 12' may be connected to the support portion 240' with the telescoping portion 250. One skilled in the art will understand that the gantry 12' need not be connected to the support portion 240' with the telescoping portion 250. In other words, the gantry 12' may be fixed to the support portion 240' in a non-moving connection. The alternative and/or additional and track portion 700 may be interconnected between the support portion 240' and a base portion 710 of the mobile cart 14'. Accordingly, the support portion 240' may move relative to the base portion generally along an axis 714 that may be parallel to the axis 274 discussed above.

The mobile base 14' may be positioned relative to the subject 28, as noted above, and the track or mobile portion 700 may be operated to move the support portion 240' relative to the fixed portion 710. Therefore, the gantry 12' that is connected to the support portion 240' may also move along the axis 714, 274. The telescoping support 250, therefore, need not be present, however, may be present, to allow movement of the gantry 12' relative to the mobile base 14'.

The track portion 700 may be substantially similar to the telescoping portion 250, as discussed above. Therefore, the track portion 700 may include a fixed track portion connected to the fixed base 710, and an intermediate frame, and a support mounting portion that is connected to the support portion 240'. Movement of the gantry 12', therefore, may be substantially equivalent to that discussed above regarding the track system 250. Accordingly, the gantry 12' and the support portion 240' may both move together due to the track portion 700 relative to the base portion 710. In addition thereto and/alternatively thereto, the gantry 12' may also move relative to the support portion 240' if the telescoping portion is also mounted between the gantry 12' and the support portion 240'.

As noted above, however, the imaging system 10', according to various embodiments, may include both the telescoping frame 250 and the track 700. Thus, the gantry 12 may move relative to the support 240' and the support 240' may move relative to the base 710. Thus, a total amount of movement, as discussed above, may be achieved by the gantry 12' being moved a first amount relative to the support portion 240' and the support portion 240' being moved a second amount relative to the base 710. The first and second amounts may be the same or different magnitudes, such as about 10 cm to about 25 cm each. Also, the telescoping frame may have a single stage and the track 700 may have a single stage, and/or more than one stage each. Thus, the gantry 12, 12' may alone move relative to the support portion 240, 240'; the support portion 240' may alone move relative to the base 710; and/or both may move to achieve a selected length of travel of the gantry along the selected axis.

The imaging system may be used to generate image data a selected length along a subject. The image may be a selected type of image, such as a two-dimensional and/or three-dimensional image. Thus, the length of the generated image may be selected and/or allowed due to the imaging system as disclosed herein.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An imaging system to acquire image data for generation of a long image of a subject, the imaging system comprising:
    a mobile base having a support portion and a mobility portion, wherein the mobility portion includes at least one moveable member configured to engage a surface and move the mobile base;
    a gantry movably connected to the support portion of the base, wherein the gantry is configured to move relative to the support portion;
    a telescoping assembly operably connected between the gantry and the support portion, wherein the telescoping assembly includes:
        a first rail member having a length between a first end and a second end, the first rail member fixed to the support portion,
        a second rail member movably connected to the first rail member and configured to translate along at least a selected portion of the length of the first rail member,
        a frame member, the second rail member fixed to the frame member,
        a third rail member fixed to the frame member, and
        a fourth rail member movable relative to the third rail member;
    a gantry mounting member configured to translate along at least the third rail member and relative to the first rail member;
    wherein the telescoping assembly is operable to support the gantry for a translation along a movement axis relative to the support portion.

2. The imaging system of claim 1, further comprising:
a x-ray emitter; and
a x-ray detector;
wherein both the x-ray emitter and the x-ray detector are configured to move within the gantry and relative to the gantry.

3. The imaging system of claim 1, further comprising:
a drive motor;
a drive member driven by the drive motor;
wherein the drive member is mounted to the gantry mounting member and fixed relative to the support portion;
wherein the drive member is driven to move the gantry mounting member.

4. The imaging system of claim 3, further comprising:
an imaging system control system included with the mobile base, wherein the imaging control system is configured to receive an input to control movement of the gantry.

5. The imaging system of claim 4, wherein the imaging control system is configured to control movement of the gantry through the drive motor.

6. The imaging system of claim 5, wherein the gantry is configured to move along the movement axis that is at least parallel to a subject axis.

7. The imaging system of claim 6, wherein the gantry is able to move at least 50 cm along the movement axis.

8. A method of providing an imaging system to acquire image data for generation of a long image of a subject, the imaging system comprising:
providing a mobile base having a support portion and a mobility portion, wherein the mobility portion includes at least one moveable member configured to engage a surface and move the mobile base;
providing a gantry connected to the support portion of the base, wherein the gantry is configured to move relative to the mobile base portion;
providing a telescoping portion including:
a first rail member having a length between a first end and a second end, the first rail member being fixed to the support portion,
connecting a second rail member to move relative to the first rail member to translate along at least a selected portion of the length of the first rail member, and
a frame member, the second rail member fixed to the frame member,
a third rail member fixed to the frame member, and
a fourth rail member movable relative to the third rail member;
providing a gantry mounting member, the fourth rail member fixed to the gantry mounting member;
wherein the telescoping portion is operable to support the gantry for an extended translation along a movement axis relative to the mobile base.

9. The method of claim 8, further comprising:
providing a x-ray emitter within the gantry;
providing a x-ray detector within the gantry; and
configuring both the x-ray emitter and the x-ray detector to move within the gantry and relative to the gantry.

10. The method of claim 8, further comprising:
providing a drive motor;
connecting a drive member to be driven by the drive motor to at least the gantry mounting member;
wherein the drive member is driven to move the gantry mounting member.

11. The method of claim 10, further comprising:
providing an imaging system control system associated with the mobile base, wherein the imaging control system is configured to receive an input to control movement of the gantry.

12. The method of claim 11, wherein the imaging control system is configured to control movement of the gantry through the drive motor.

13. The method of claim 12, further comprising:
providing the gantry to move along the movement axis that is at least parallel to a subject axis.

14. The method of claim 13, further comprising:
providing the gantry to move at least 50 cm along the movement axis.

15. The method of claim 13, further comprising:
positioning the provided telescoping portion between the support portion and the gantry;
configuring the frame member to move relative to the support portion and the gantry via the provided telescoping portion.

16. The method of claim 13, further comprising:
positioning the provided telescoping portion between the support portion and the gantry;
configuring the gantry to move relative to the support portion via the provided telescoping portion.

17. The method of claim 13, further comprising:
wherein providing the telescoping portion further includes providing a first telescoping portion between the gantry and the frame member and providing a second telescoping portion between the frame member and the mobile base;
configuring the support frame member to move relative to the mobile base via the provided telescoping portion; and
configuring the gantry to move relative to the frame member via the provided telescoping portion.

18. An imaging system to acquire image data for generation of a long image of a subject having a movement assembly, the movement assembly comprising:
a first rail member having a length between a first end and a second end, the first rail member fixed to a support portion,
a second rail member movably connected to the first rail member and configured to translate along at least a selected portion of the length of the first rail member,
a frame member, the second rail member fixed to the frame member,
a third rail member fixed to the frame member, and
a fourth rail member movable relative to the third rail member;
a gantry mounting member configured to translate along at least the third rail member and relative to the first rail member the fourth rail member fixed to the gantry mounting member;
wherein the movement assembly is configured to be connected between a gantry and at least one of the support portion or a mobile base;
wherein the movement assembly is operable to support the gantry for an extended translation along a movement axis relative to the support portion.

19. The system of claim 18, further comprising:
the mobile base having the support portion and a mobility portion, wherein the mobility portion includes at least one moveable member configured to engage a surface and move the mobile base; and the gantry movably configured to be connected to the gantry mounting member, wherein the gantry is configured to move relative to the support portion via the movement assembly.

20. The system of claim 19, further comprising:
a drive motor;
a drive member driven by the drive motor;
wherein the drive member is mounted to the gantry mounting member and fixed relative to the support portion;
wherein the drive member is driven to move the gantry mounting member and the second rail member.

21. The system of claim 20, wherein the gantry is able to move at least 70 cm along a movement axis via the movement system while being driven by the drive motor.

* * * * *